United States Patent [19]

Meyer

[11] Patent Number: 4,883,651

[45] Date of Patent: Nov. 28, 1989

[54] DEODORANT

[76] Inventor: Holger Meyer, Elfenbeinweg 15, 2000 Hamburg 65, Fed. Rep. of Germany

[21] Appl. No.: 191,978

[22] Filed: May 9, 1988

[30] Foreign Application Priority Data

May 14, 1987 [DE] Fed. Rep. of Germany ....... 3716129

[51] Int. Cl.$^4$ .......................... A61K 7/32; A61K 9/12; A61L 9/01
[52] U.S. Cl. ........................................ 424/47; 424/65; 424/76.1
[58] Field of Search ............................... 424/65, 195.1

[56] References Cited

U.S. PATENT DOCUMENTS 3,743,717 7/1973 Okano ..................................... 424/65
4,501,730 2/1985 Torii et al. ........................ 424/195.1

FOREIGN PATENT DOCUMENTS 2422780 11/1975 Fed. Rep. of Germany ........ 424/65

Primary Examiner—Dale R. Ore
Attorney, Agent, or Firm—Miller & Gibbons

[57] ABSTRACT

A deodorant is described which contains an extract of Coffea arabinensis which optionally can be combined with an extract of Thea sinensis. These extracts have deodorizing characteristics, which can be further considerably increased by combination with extracts of Urtica and knotgrass. The inventive deodorant is in particular suitable for room air improving products and body deodorants.

2 Claims, No Drawings

DEODORANT

BACKGROUND OF INVENTION

The invention relates to a deodorant, particularly suitable for use in conjunction with room air improving products and body deodorants.

It has surprisingly been found that extracts of Coffea arabinensis and/or Thea sinensis have deodorizing characteristics and that these characteristics can be further considerably increased by combination with extracts of Urtica as well as knotgrass.

In DE-OS No. 16 17 598 a beauty care product for skin treatment on an aqueous or fatty basis is disclosed which comprises an aqueous or fatty tea extract. However, there is no mention that the beauty care product or the tea extract included therein have any deodorizing characteristics.

OBJECT OF THE INVENTION

Therefore it is an object of this invention to provide deodorants with good deodorizing characteristics on the basis of conventional deodorant formulations comprising active ingredients obtained from natural sources.

It is a further object of this invention to provide deodorants with further improved deodorizing characteristics by including a synergistic combination of active ingredients obtained from natural sources.

These and further objects will become apparent as the description of the invention proceeds.

DETAILED DESCRIPTION OF INVENTION

The invention is directed to a deodorant which is characterized in that it contains an extract of Coffea arabinensis. Optionally the deodorant can also contain an extract of Thea sinensis. According to a preferred embodiment the inventive deodorant additionally contains an extract of Urtica and/or knotgrass (family of Polygonaceae).

The production of the extracts to be used in accordance with the invention takes place through extraction of the plants or plant parts to be used according to the invention by conventional extracton processes. With regards to the appropriate conventional extraction processes, such as maceration, vortex extraction, countercurrent extraction, percolation, repercolation, evacolation (extraction under reduced pressure) and diacolation, which are known to the Expert and which can all in principle be used, reference is made for reasons of simplicity e.g. to Hagers Handbuch der Pharmazeutischen Praxis, fourth edition, vol. 7, Springer-Verlag, Berlin-Heidelberg-New York 1971. The solvents for performing the extraction can be organic solvents, water (preferably hot water at a temperature of more than 80° C. and in particular more than 95° C.) or mixtures of organic solvents and water, particularly low molecular weight alcohols with more or less high water contents (usually extraction with these mixtures takes place at about room temperature). Ethanol-water mixtures (60:40) are particularly suitable for the inventive purposes.

For the extraction of Coffea arabinensis, raw coffee (unroasted coffee beans) are comminuted and namely to a particle size roughly corresponding to coarse filter coffee. For the extraction of Thea sinensis, correspondingly dried or also undried tea leaves are comminuted with a mill or a chopping machine to give a coarse powder. Urtica (stinging nettles) and knotgrass, such as spinach and rhubarb are prepared in the same way for extraction. In the case of stinging nettles and rhubarb, the complete plant can be used for extraction purposes.

The extraction can take place up to any desired degree of extraction (provided that it is economically acceptable), but is normally carried out up to exhaustion, which gives an extract normally having a solids content of approximately 3 to 5% by weight. It is usually advantageous for the further processing of the thus obtained extract to adjust a lower solids content of approximately 1.5% by weight by redilution with water. The thus obtained thin extract is clarified and carefully concentrated in vacuo, in that the ethanol contained in the preferred extraction medium (ethanolwatermixture) is distilled off, so that it can be used for further extraction processes. Subsequently sufficient propylene glycol is added to the concentrated extract freed from ethanol so that the solids content is again approximately 1.5% by weight and the solvent preferably comprises approximately 40% propylene glycol and 60% water. This extract is then used as a component for room air improving products or body deodorant formulations or other deodorizing agent formulations.

The described production of the extract to be used in the deodorizing agent formulations can obviously be varied by the Expert in the most varied ways as a function of the intended use. However, this does not constitute a problem for the Expert, so that no explanations are needed.

The inventively used extracts contain mucilages, tannic acids and vegetable acids, as well as the in each case type-typical constituents of the plant types used. Without wishing to be bound by a theory, it is assumed that the binding of the olfactory components initially takes place as absorption in the usually highly hygroscopic medium of the conventional basic preparation of the deodorant. There is subsequently probably a clathrate-like and also chemical binding to the constituents, such as starch and tannic acid. When used as a body deodorant, the additional effects of the other plant constituents come into action. It is probably essentially the action of phytosterins, which are both secretion-inhibiting and antioxidative. This considerably reduces the quantity of malodorous substances given off (action on the apocrine glands) and their oxidative decomposition is reduced. Particular significance can probably also be attached to the chlorogenic acid extracted from the raw coffee, which acts bacteriostatically and therefore prevents the bacterial decomposition of the olfactory component as the main cause of body odour. The high substantivity, i.e. the high absorptive power of this naturally antibacterial substance ensures a long lasting deodorizing effect, which admittedly can also be revealed with the pure substance, but in the overall preparation according to the invention in the presence of the other constituents has a much better action.

It has inventively surprisingly been found that deodorants containing two or more of the inventively usable extracts reveal a marked synergism of the deodorizing action, i.e. the action far exceeds the action of each of the individual components. Thus, according to a highly preferred embodiment of the invention, an extract of *Coffea arabinensis* is combinded with an extract of Urtica (*Urtica mayor, Urtica dioica*) and/or knotgrasses, such as spinach and rhubarb. In addition an extract of Thea sinensis can also be added (see above).

The extracts and extract combinations to be used according to the invention serve as constituents in conventional deodorant formulations, the quantity used being a function of the intended use and the desired effectiveness. Usually 0.5 to 20% by weight and preferably 1 to 10% by weight of the inventive extracts are included in the conventional deodorant formulations. Conventional deodorant formulations are known to the Expert. Reference is e.g. made to Karlheinz Schrader, Grundlagen und Rezepturen der Kosmetika, 1979, Dr. A. Huethig Verlag, Heidelberg and G. A. Nowak, Die kosmetischen Präparate, second edition, 1975, Verlag für chem. Industrie H. Ziolkowsky, Augsburg.

EXAMPLE 1

5000 g of drug (comminuted raw coffee) were exhaustively extracted with an alcohol-water mixture. The thin extract was clarified and carefully concentrated in vacuo. This was followed by filling with propylene glycol, so that the thin extract had a solids content of approximately 1.5% by weight and a propylene glycol content of approximately 40% by weight. The extract was a green-blue, clear liquid, which was almost clear-soluble in propylene glycol.

Various tests were carried out with the thus obtained extract after producing a 5% extract solution by filling with water. The following tests were carried out:
1. The hands and other body parts were smeared with
   a) Romadours and Limburger cheese,
   b) onions,
   c) garlic and
   d) burnt tobacco residues from a pipe.

The odours disappeared immediately after spraying with the inventive active substance solution.

2. Sports shoes and socks smelling of decomposed perspiration were sprayed with the active substance solution and the odour was immediately eliminated.

3. The active substance solution was sprayed into WC's against fecal odour and the odours were again immediately eliminated.

4. Unpacked pieces of cheese (Appenzell, Limburger and Gorgonzola) were placed in a refrigerator and alongside them a non-woven piece of fabric impregnated with the active substance solution. The refrigerator remained odourless.

The following examples give a few typical preparations (in % by weight) containing the extracts proposed by the invention.

EXAMPLE 2

Formulation for a room air improving product:
5% extract
3% triethylene glycol
3% 1,2-propylene glycol
5% isopropanol
4% water
80% propellant gas The extract has a solids content of approximately 1.5% by weight and the solvent mixture consists of 40% by weight propylene glycol and 60% by weight water. The propellant gas can be constituted by conventional propellant gases, such as chlorofluorohydrocarbons (Frigens), carbon dioxide, etc.

EXAMPLE 3

Formulation for a room air improving product for spraying:
2 to 10% extract
3% triethylene glycol
3% dipropylene glycol
remainder ad 100% water.

EXAMPLE 4

Formulation for a roll-on deodorant:
3% polyglycol 400
2% extract
30% ethanol
15% water
50% methyl cellulose-based thickener.

EXAMPLE 5

Formulation for a deodorant spray:
1% extract
4% water
25% ethanol
70% propellant gas With regards to the extracts and propellant gases used in examples 3 to 5, reference should be made to the explanations in example 2.

I claim:

1. A deodorant composition comprising an effective amount of an extract of coffee arabinensis and an extract of rhubarb.

2. A deodorant composition according to claim 1 wherein said composition is a room air deodorant or a body deodorant.

* * * * *